(12) United States Patent
Ford et al.

(10) Patent No.: US 9,650,479 B2
(45) Date of Patent: *May 16, 2017

(54) DENSE ARTICLES FORMED FROM TETRAFLUOROETHYLENE CORE SHELL COPOLYMERS AND METHODS OF MAKING THE SAME

(71) Applicants: W. L. Gore & Associates, Inc., Newark, DE (US); W. L. Gore & Associates GmbH, Putzbrunn (DE)

(72) Inventors: Lawrence A. Ford, München (DE); Michael E. Kennedy, Oxford, PA (US); Shaofeng Ran, Kennett Square, PA (US); Todd S. Sayler, Bear, DE (US); Gregory J. Shafer, Oxford, PA (US)

(73) Assignees: W. L. Gore & Associates, Inc., Newark, DE (US); W. L. Gore & Associates GmbH, Putzbrunn (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/577,566

(22) Filed: Dec. 19, 2014

(65) Prior Publication Data
US 2015/0111031 A1 Apr. 23, 2015

Related U.S. Application Data

(63) Continuation-in-part of application No. 12/408,153, filed on Mar. 20, 2009, now Pat. No. 9,040,646, (Continued)

(51) Int. Cl.
| | |
|---|---|
| *C08F 259/08* | (2006.01) |
| *C08F 214/26* | (2006.01) |
| *B32B 27/06* | (2006.01) |
| *B32B 27/32* | (2006.01) |
| *C08J 5/18* | (2006.01) |
| *A61L 27/16* | (2006.01) |
| *A61L 27/50* | (2006.01) |
| *A61L 27/56* | (2006.01) |
| *A61L 31/04* | (2006.01) |
| *A61L 31/14* | (2006.01) |
| *B29C 55/00* | (2006.01) |
| *C08J 9/00* | (2006.01) |

(Continued)

(52) U.S. Cl.
CPC .............. *C08J 5/18* (2013.01); *A61L 27/16* (2013.01); *A61L 27/26* (2013.01); *A61L 27/34* (2013.01); *A61L 27/507* (2013.01); *A61L 27/56* (2013.01); *A61L 29/041* (2013.01); *A61L 29/049* (2013.01); *A61L 29/085* (2013.01); *A61L 31/041* (2013.01); *A61L 31/048* (2013.01); *A61L 31/10* (2013.01); *A61L 31/146* (2013.01); *B29C 44/5627* (2013.01); *B29C 55/005* (2013.01); *B32B 27/06* (2013.01); *B32B 27/322* (2013.01); *C08F 259/08* (2013.01); *C08J 9/00* (2013.01); *B29K 2027/00* (2013.01); *B29K 2027/12* (2013.01); *B29K 2027/18* (2013.01); *B29K 2105/04* (2013.01); *B32B 2250/00* (2013.01); *B32B 2250/24* (2013.01); *B32B 2307/72* (2013.01); *B32B 2327/18* (2013.01); *B32B 2437/00* (2013.01); *B32B 2439/00* (2013.01); *B32B 2535/00* (2013.01); *B32B 2581/00* (2013.01); *C08F 214/26* (2013.01); *C08J 2207/02* (2013.01); *C08J 2327/18* (2013.01); *Y10T 428/1376* (2015.01); *Y10T 428/28* (2015.01); *Y10T 428/31544* (2015.04)

(58) Field of Classification Search
CPC ............................. C08F 259/08; C08L 27/18
See application file for complete search history.

(56) References Cited

U.S. PATENT DOCUMENTS

| | | |
|---|---|---|
| 3,196,194 A | 7/1965 | Ely, Jr. et al. |
| 3,654,210 A | 4/1972 | Kuhls et al. |

(Continued)

FOREIGN PATENT DOCUMENTS

| | | |
|---|---|---|
| EP | 0352749 | 1/1990 |
| EP | 1192957 A2 | 4/2002 |

(Continued)

OTHER PUBLICATIONS

Fluoroplastics—vol. 1: Non-Melt Processible Fluoroplastics; Williams Andrew, Inc. ; Norwich, NY at p. 19 (2000).
International Standard ISO 12086-1: 2006, Fluoropolymer dispersions and mounding and extrusion materials; Part 1: Designation system and basis for specifications, Geneva, Switzerland (2006).
Drobny, Technology of Fluoropolymers Second Edition; General Chemistry (7 pages).
Ebnesajjad, Sina; Fluoproplastics, PCL Handbook Series, vol. 1, Non-Melt Processible Fluoroplastics, The Definitive User's Guide and Databank; pp. 51-52.
2010 Fluorotherm Polymers, Inc. powered by WebiMax.com http://Flurotherm.com/Properties-Physical.asp Comparison of Materials, Typical Properties of Fluoropolymers; 2010.

(Continued)

*Primary Examiner* — Nicole M Buie-Hatcher
(74) *Attorney, Agent, or Firm* — Amy L. Miller

(57) ABSTRACT

A tetrafluoroethylene (TFE) copolymer film having a first endotherm between about 50° C. and about 300° C., a second endotherm between about 320° C. and about 350° C., and a third endotherm between about 350° C. and about 400° C. is provided. In exemplary embodiments, the third endotherm is approximately 380° C. In some embodiments, the second endotherm is between about 320° C. and about 330° C. or between about 330° C. and about 350° C. TFE copolymer films have a methane permeability less than about 20 μg*micron/cm²/min. In addition, the dense articles have a void volume of less than about 20%. Methods for dense articles from core shell tetrafluoroethylene copolymers are also provided. The dense articles exhibit improved physical and mechanical properties such as adhesion and barrier properties.

29 Claims, 8 Drawing Sheets

Related U.S. Application Data which is a continuation-in-part of application No. 11/906,877, filed on Oct. 4, 2007, now Pat. No. 8,637,144.

(51) Int. Cl.

| | |
|---|---|
| *B29C 44/56* | (2006.01) |
| *A61L 27/26* | (2006.01) |
| *A61L 27/34* | (2006.01) |
| *A61L 29/04* | (2006.01) |
| *A61L 29/08* | (2006.01) |
| *A61L 31/10* | (2006.01) |
| *B29K 27/12* | (2006.01) |
| *B29K 27/00* | (2006.01) |
| *B29K 27/18* | (2006.01) |
| *B29K 105/04* | (2006.01) |

(56) References Cited

U.S. PATENT DOCUMENTS

| | | | |
|---|---|---|---|
| 3,655,611 A | 4/1972 | Mueller | |
| 3,929,950 A | 12/1975 | Nakamura et al. | |
| 3,953,566 A | 4/1976 | Gore | |
| 4,016,345 A | 4/1977 | Holmes | |
| 4,036,802 A | 7/1977 | Poirer | |
| 4,038,231 A | 7/1977 | Downer | |
| 4,129,618 A | 12/1978 | Downer | |
| 4,187,390 A | 2/1980 | Gore | |
| 4,194,041 A | 3/1980 | Gore | |
| 4,381,384 A | 4/1983 | Khan | |
| 4,391,940 A | 7/1983 | Kuhls | |
| 4,469,744 A | 9/1984 | Grot | |
| 4,518,650 A | 5/1985 | Grot | |
| RE31,907 E | 6/1985 | Poirer | |
| 4,576,869 A | 3/1986 | Malhotra | |
| 4,623,670 A | 11/1986 | Mutoh et al. | |
| 4,675,380 A | 6/1987 | Buckmaster | |
| 4,742,122 A | 5/1988 | Buckmaster | |
| 4,770,927 A | 9/1988 | Effenberger | |
| 4,780,490 A | 10/1988 | Mizuno et al. | |
| 4,792,594 A | 12/1988 | Gangal | |
| 4,824,511 A | 4/1989 | Hattmati | |
| 4,830,062 A | 5/1989 | Yamamoto et al. | |
| 4,837,267 A | 6/1989 | Malhotra | |
| 4,840,998 A | 6/1989 | Shimizu | |
| 4,879,362 A | 11/1989 | Morgan | |
| 4,904,726 A | 2/1990 | Morgan | |
| 4,952,630 A | 8/1990 | Morgan | |
| 4,952,636 A | 8/1990 | Morgan | |
| 5,064,593 A | 11/1991 | Tamaru et al. | |
| 5,188,764 A | 2/1993 | Shimizu et al. | |
| 5,230,937 A | 7/1993 | Effenbercier | |
| 5,266,639 A | 11/1993 | Chapman | |
| 5,374,473 A | 12/1994 | Knox et al. | |
| 5,374,683 A | 12/1994 | Morgan | |
| 5,397,829 A | 3/1995 | Morgan | |
| 5,464,904 A | 11/1995 | Chapman | |
| 5,494,752 A | 2/1996 | Shimizu | |
| 5,506,281 A | 4/1996 | Muhlbauer | |
| 5,523,346 A * | 6/1996 | Wu | C08F 214/18 524/805 |
| 5,547,551 A | 8/1996 | Bahar | |
| 5,547,761 A | 8/1996 | Chapman | |
| 5,599,614 A | 2/1997 | Bahar | |
| 5,635,041 A | 6/1997 | Bahar | |
| 5,637,663 A | 6/1997 | Anolick | |
| 5,681,402 A | 10/1997 | Ichinose | |
| 5,731,394 A | 3/1998 | Treat | |
| 5,756,620 A | 5/1998 | Aten | |
| 5,861,324 A | 1/1999 | Ichinose | |
| 5,898,042 A | 4/1999 | Sawada et al. | |
| 5,922,425 A | 7/1999 | Greuel | |
| 5,922,468 A | 7/1999 | Huesmann | |
| 5,925,705 A | 7/1999 | Araki | |
| 5,972,449 A | 10/1999 | Chung | |
| 6,025,092 A | 2/2000 | Doyle | |
| 6,060,167 A | 5/2000 | Morgan | |
| 6,071,600 A | 6/2000 | Rosenmayer | |
| 6,103,361 A | 8/2000 | Batzar | |
| 6,107,423 A | 8/2000 | Wheland | |
| 6,114,028 A | 9/2000 | Muchin | |
| 6,114,452 A | 9/2000 | Schmiegel | |
| 6,127,486 A | 10/2000 | Burger | |
| 6,133,389 A | 10/2000 | Anolick | |
| 6,136,933 A | 10/2000 | Jones | |
| 6,140,410 A | 10/2000 | Kolouch | |
| 6,140,436 A | 10/2000 | Doyle | |
| 6,143,675 A | 11/2000 | McCollam et al. | |
| 6,156,453 A | 12/2000 | Shimizu et al. | |
| 6,166,138 A | 12/2000 | Kolouch | |
| 6,177,196 B1 | 1/2001 | Brothers | |
| 6,177,533 B1 | 1/2001 | Woodward | |
| 6,191,208 B1 | 2/2001 | Takahashi | |
| 6,197,904 B1 | 3/2001 | Gangal | |
| 6,211,319 B1 | 4/2001 | Schmiegel | |
| 6,221,970 B1 | 4/2001 | Morken | |
| 6,228,963 B1 | 5/2001 | Wheland | |
| 6,232,372 B1 | 5/2001 | Brothers | |
| 6,248,435 B1 | 6/2001 | Leck | |
| RE37,307 E | 8/2001 | Bahar | |
| 6,281,296 B1 | 8/2001 | MacLachlan | |
| 6,287,702 B1 | 9/2001 | Kolouch | |
| 6,291,054 B1 | 9/2001 | Thomas | |
| 6,300,445 B1 | 10/2001 | Hung | |
| 6,312,814 B1 | 11/2001 | Kolouch | |
| 6,359,030 B1 | 3/2002 | Tsuda | |
| RE37,656 E | 4/2002 | Bahar | |
| RE37,701 E | 5/2002 | Bahar | |
| 6,395,848 B1 | 5/2002 | Morgan | |
| 6,403,213 B1 | 6/2002 | Huesmann | |
| 6,403,758 B1 | 6/2002 | Loomis | |
| 6,416,698 B1 | 7/2002 | Mertdogan | |
| 6,423,798 B2 | 7/2002 | Wheland | |
| 6,429,258 B1 | 8/2002 | Morgan | |
| 6,472,594 B1 | 10/2002 | Ichinose | |
| 6,486,280 B1 | 11/2002 | Anolick | |
| 6,509,429 B1 | 1/2003 | Kitaichi | |
| 6,518,349 B1 | 2/2003 | Felix | |
| 6,518,381 B2 | 2/2003 | Kobayashi | |
| 6,538,058 B2 | 3/2003 | Kobayashi | |
| 6,541,589 B1 | 4/2003 | Baillie | |
| 6,551,708 B2 | 4/2003 | Tsuda | |
| 6,582,628 B2 | 6/2003 | Kondo | |
| 6,592,977 B2 | 7/2003 | Thomas | |
| 6,638,999 B2 | 10/2003 | Bish | |
| 6,689,833 B1 | 2/2004 | Bidstrup | |
| 6,730,762 B2 | 5/2004 | Lousenberg | |
| 6,750,294 B2 | 6/2004 | Sugiyama | |
| 6,761,964 B2 | 7/2004 | Tannenbaum | |
| 6,770,404 B1 | 8/2004 | Wheland | |
| 6,803,419 B2 | 10/2004 | Tsuda | |
| 6,803,437 B2 | 10/2004 | Kobayashi | |
| 6,806,332 B2 | 10/2004 | Royer | |
| 6,822,059 B2 | 11/2004 | Buckanin | |
| 6,822,060 B2 | 11/2004 | Kobayashi | |
| 6,824,930 B1 | 11/2004 | Wheland | |
| 6,833,418 B2 | 12/2004 | Tan | |
| 6,841,594 B2 | 1/2005 | Jones | |
| 6,870,020 B2 | 3/2005 | Aten | |
| 6,914,105 B1 | 7/2005 | Charpentier | |
| 6,921,606 B2 | 7/2005 | Sassa et al. | |
| 6,956,078 B2 | 10/2005 | Cavanaugh | |
| 7,049,365 B2 | 5/2006 | Uschold | |
| 7,063,839 B2 | 6/2006 | Royer | |
| 7,064,170 B2 | 6/2006 | Kaspar | |
| 7,084,225 B2 | 8/2006 | Baillie | |
| 7,521,010 B2 | 4/2009 | Kennedy et al. | |
| 7,531,611 B2 | 5/2009 | Sabol et al. | |
| 7,829,170 B1 | 11/2010 | Bowen et al. | |
| 8,012,555 B2 | 9/2011 | Zumbrum | |
| 8,637,144 B2 | 1/2014 | Ford | |
| 8,911,844 B2 | 12/2014 | Ford | |
| 9,040,646 B2 | 5/2015 | Ford | |

(56) References Cited

U.S. PATENT DOCUMENTS

| | | |
|---|---|---|
| 2005/0064195 A1 | 3/2005 | Kobayashi |
| 2005/0220848 A1 | 10/2005 | Bates |
| 2006/0041091 A1 | 2/2006 | Chang |
| 2006/0047311 A1* | 3/2006 | Lutz .................. A01K 91/00 606/228 |
| 2006/0148912 A1 | 7/2006 | Katsurao et al. |
| 2006/0233990 A1 | 10/2006 | Humphrey |
| 2009/0093602 A1 | 4/2009 | Ford |
| 2013/0231733 A1 | 9/2013 | Knisley |

FOREIGN PATENT DOCUMENTS

| | | |
|---|---|---|
| EP | 1 201 689 | 5/2002 |
| EP | 1 746 130 | 1/2007 |
| GB | 2 337 991 | 12/1999 |
| JP | 56 92943 | 7/1981 |
| JP | 03-069926 B | 11/1991 |
| JP | 05279506 A * | 10/1993 |
| JP | 8-26102 | 3/1996 |
| JP | 10-243976 | 12/1997 |
| JP | 11-240917 | 9/1999 |
| JP | 11-240918 | 9/1999 |
| JP | 2003-192815 | 7/2003 |
| JP | 2005-306033 | 11/2005 |
| JP | 2007-514481 | 6/2007 |
| JP | 2010-540749 | 12/2010 |
| JP | 2012036266 A * | 2/2012 |
| WO | WO94/04334 | 3/1994 |
| WO | WO97/36952 | 10/1997 |
| WO | WO98/07450 | 2/1998 |
| WO | WO99/07307 | 2/1999 |
| WO | WO2007/005361 | 1/2007 |
| WO | WO2007/015961 | 2/2007 |
| WO | WO2009/045423 | 4/2009 |
| WO | WO2009045423 | 4/2009 |
| WO | WO2010-107494 | 9/2010 |

OTHER PUBLICATIONS

Ebnesajjad, S. (2000), Fluoroplastics, vol. 1—Non-Melt Processible Fluoroplastics. William Andrew Publishing/Plastics Design Library. Preface and Chapter 3, pp. 33-38. Online version available at: http://wvvw.knovel.com/we/portal/browse/display?_EXT_KNOVEL_DISPLAY_bookid=64&VerticalID-0.

"Olefin (chemical compound)", Encylcopedia Brittanica, Encyclopedia Brittancia Online, Encylcopedia Brittanica Inc., 2013.

International Search Report PCTUS2015063603 dated Mar. 11, 2016, 7 pages.

* cited by examiner

DENSE ARTICLES FORMED FROM TETRAFLUOROETHYLENE CORE SHELL COPOLYMERS AND METHODS OF MAKING THE SAME

FIELD

The present invention relates generally to tetrafluoroethylene (TFE) core shell copolymers, and more specifically, to dense articles formed from TFE core shell copolymers. Methods of making dense articles utilizing TFE core shell copolymers are also provided.

BACKGROUND

Barrier films are used in a wide variety of technologies, including medical and commercial devices. For example, barrier films find use in short and long term implantable medical devices, seals, gaskets, blood contact surfaces, bags, containers, and fabric liners. In addition to good barrier properties, barrier films should have good mechanical properties and be thermally stable. Monolithic, multi-component, and multilayered barrier films have been constructed as barrier materials, but have not provided a combination of thermal stability, strength, and barrier properties.

Polytetrafluoroethylene (PTFE) has been evaluated for use as barrier films. The use of PTFE is advantageous in that it can be used in harsh chemical environments and over a broad range of temperatures. For example, PTFE has exhibited utility as a material for use in harsh chemical environments where other polymers quickly degrade. PTFE also has a useful temperature range from as high as about 260° C. to as low about −273° C. However, PTFE barrier films are characterized by poor mechanical properties such as low tensile strength, poor cold flow resistance or creep resistance, poor cut-through and abrasion resistance, and a general poor mechanical integrity that precludes its consideration in many materials engineering applications.

Low porosity PTFE articles have been made through the use of a skiving process in which solid PTFE films are split or shaved from a thicker preformed article. These PTFE articles are characterized by low strength, poor cold flow resistance, and poor load bearing capabilities in both the length and width directions of the film. Processes such as ram extrusion of PTFE fine powder have also been used to produce low porosity PTFE articles; however, such films also possess relatively poor mechanical characteristics. Attempts have also been made to strengthen the low porosity PTFE films by stretching in the length dimension. However, strength gains are minimal and, by the nature of the process, are achieved in only a single dimension, thus greatly minimizing the utility of the film.

A expanded polytetrafluoroethylene (ePTFE) film may be produced by a process taught in U.S. Pat. No. 3,953,566, to Gore. The porous ePTFE formed by the process has a microstructure of nodes interconnected by fibrils, demonstrates higher strength than unexpanded PTFE, and retains the chemical inertness and wide useful temperature range of unexpanded PTFE. However, such an expanded PTFE film is porous and therefore cannot be used as a barrier layer to low surface tension fluids since such fluids with surface tensions less than 50 dyne-cm pass through the pores of the membrane.

Compressed ePTFE articles in which a platen press was used to densify a thin sheet of ePTFE with and without heat are also taught in U.S. Pat. No. 3,953,566 to Gore. However, cold flow occurred in the press, non-uniform parts resulted, and a density of over 2.1 g/cc was not achieved. Accordingly, the utility of the ePTFE sheet as a barrier film was limited.

Thus, there exists a need in the art for a TFE-based barrier film that demonstrates improved barrier performance (such as evidenced by a resistance to methane permeation), improved physical and mechanical performance (such as low creep), and high matrix tensile strength.

SUMMARY

One embodiment of the invention relates to a dense article that includes a tetrafluoroethylene (TFE) copolymer film having a first endotherm below about 300° C., a second endotherm between about 320° C. and about 350° C., and a third endotherm between about 350° C. and about 400° C. In some embodiments, the second endotherm may be between about 320° C. and about 330° C. or between about 330° C. and about 350° C. The first endotherm may occur between about 50° C. and about 300° C. In exemplary embodiments, the third endotherm is approximately 380° C. The TFE copolymer film possesses a methane permeability less than about 20 µg*micron/cm$^2$/min. In addition, the dense articles have a void volume of less than about 20%.

A second embodiment of the invention relates to a process for making a dense article that includes densifying a TFE copolymer film to form a dense TFE copolymer film (i.e., a dense article). The TFE copolymer film has a first endotherm between about 50° C. to about 300° C., a second endotherm between about 320° C. and about 350° C., and a third endotherm between about 350° C. and about 400° C. The densification of the TFE copolymer film may occur at a temperature up to about 400° C. In one embodiment, the densification of the TFE copolymer film occurs at a temperature below the first endotherm. In another embodiment, the densification occurs at a temperature above the first endotherm. In yet another embodiment, the densification occurs at a temperature above the second endotherm. In a further embodiment, the densification occurs at a temperature between the first endotherm and the second endotherm. In another embodiment, the densification occurs at a temperature between the second endotherm and the third endotherm. The process may also include heat treating the TFE copolymer film prior to and/or after densifying the TFE copolymer film.

A third embodiment of the invention relates to a process for making a dense article that includes (1) densifying a TFE copolymer film to form a dense TFE copolymer film and (2) stretching the dense TFE copolymer film to form a dense article. The TFE copolymer film has a first endotherm below about 300° C. (e.g., from about 50° C. to about 300° C.), a second endotherm between about 320° C. and about 350° C., and a third endotherm between about 350° C. and about 400° C. In exemplary embodiments, the third endotherm is approximately 380° C. The dense TFE copolymer film may be stretched at a temperature between the first endotherm and about 400° C. In one embodiment, the stretching occurs at a temperature above the first endotherm. In another embodiment, the stretching occurs at a temperature above the second endotherm. In yet another embodiment, the stretching occurs at a temperature between the first endotherm and the second endotherm. In a further embodiment, the stretching occurs at a temperature between the second endotherm and the third endotherm. The method may further include heat treating the TFE copolymer film prior to and/or after densifying the TFE copolymer film and/or prior to and/or after stretching the densified TFE copolymer film.

A fourth embodiment of the invention relates to a laminate that includes (1) a dense article and (2) a substrate. The dense article may be a dense article that is a TFE copolymer film that has been compressed into a dense TFE copolymer film or dense article that is a TFE copolymer film that has been compressed and subsequently stretched into a dense article. The TFE copolymer films have a first endotherm from about 50° C. to about 300° C., a second endotherm between about 300° C. and about 350° C., and a third endotherm between about 350° C. and about 400° C. The substrate is not particularly limiting, and may include fluorinated ethylene propylene (FEP), perfluoroalkoxy alkane (PFA), polytetrafluoroethylene (PTFE), a polymer of tetrafluoroethylene, hexafluoropropylene, and vinylidene fluoride (THV), polyurethanes, polyamides, ethylene vinyl alcohol (EVOH), polyvinyl chloride (PVC), a metallic sheet, an inorganic sheet, or a pressure sensitive adhesive.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

GLOSSARY

Figure 1:
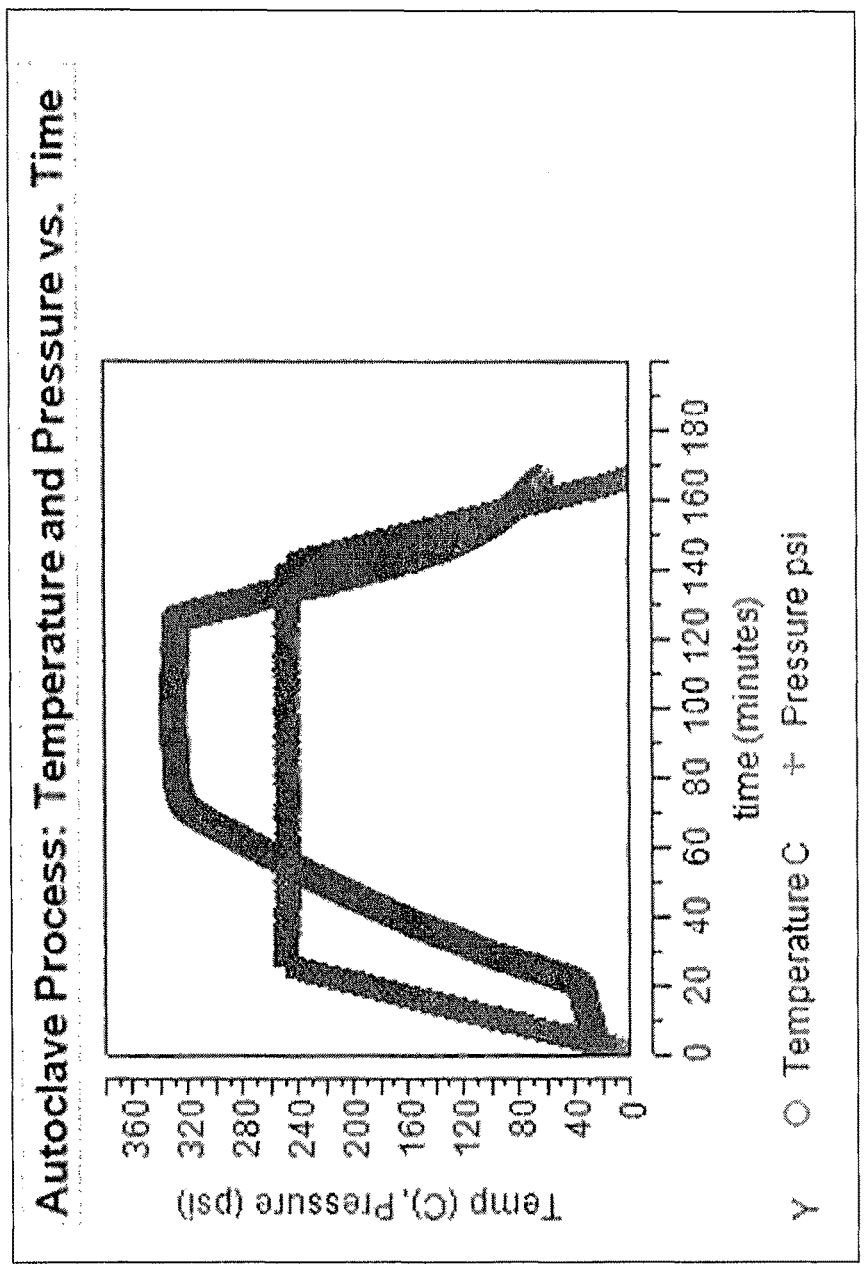
FIG. 1 is a graphical illustration of temperature and pressure vs. time for an autoclave process used in densifying a TFE-VDF copolymer according to at least one embodiment of the invention.

The term "comonomer" as used herein is meant to denote any comonomer present within the core shell tetrafluoroethylene copolymer other than the tetrafluoroethylene monomer.

As used herein, the phrase "substantially only TFE monomers" is meant to denote that the shell portion in the core shell TFE copolymer contains (1) TFE monomers or (2) TFE monomers and an unquantifiable amount (trace amount) of comonomer.

As used herein, the term "copolymer" is meant to describe a reaction product of TFE monomers and at least one comonomer where the comonomer is present in the copolymer in an amount of at least 3.0% by weight polymerized units based on the total weight of the TFE copolymer.

As used herein, the terms "dense" and "densified" are meant to describe an article that has a void volume less than about 20%.

As used, herein, the terms "width" and "length" are analogous to the x-direction and y-direction, respectively.

As used herein, the term "lubricant" is meant to describe a processing aid that includes, and in some embodiments, consists of, an incompressible fluid that is not a solvent for the polymer at processing conditions. The fluid-polymer surface interactions are such that it is possible to create an homogenous mixture.

DESCRIPTION OF THE INVENTION

Persons skilled in the art will readily appreciate that various aspects of the present disclosure can be realized by any number of methods and apparatus configured to perform the intended functions. It should also be noted that the accompanying figures referred to herein are not necessarily drawn to scale, but may be exaggerated to illustrate various aspects of the present disclosure, and in that regard, the drawing figures should not be construed as limiting.

The present invention relates to dense articles formed from, TFE core shell copolymers. This disclosure also relates to processes for making dense articles from core shell TFE copolymers. The dense articles exhibit improved physical and mechanical properties including both adhesion and barrier properties. The terms "TFE copolymer", "TFE core shell copolymer", and "core shell TFE copolymer" may be used interchangeably herein. Additionally, the terms "dense" and "densified" may be used interchangeably in this application.

A tetrafluoroethylene (TFE) copolymer having a core shell configuration is formed by a process in which tetrafluoroethylene monomers are copolymerized with at least one comonomer other than TFE. As used herein, the term "comonomer" is meant to describe a monomer within the TFE copolymer other than tetrafluoroethylene. The comonomer may be an ethylenically unsaturated monomer having a reactivity with TFE so as to enable polymerization with the TFE monomers. For example the comonomer may be a perfluoroalkyl ethylene monomer, such as perfluorobutylethylene (PFBE), perfluorohexylethylene (PFHE), and perfluoro-octylethylene (PFOE), or it may be a perfluoroalkyl vinyl ether monomer such perfluoro(methyl vinyl ether) (PMVE), perfluoro(ethyl vinyl ether) (PEVE), and perfluoro (propyl vinyl ether) (PPVE).

The comonomer may alternatively, or also, be an olefin such as ethylene, propylene or isobutylene, a fluorinated monomer such as chlorotrifluoroethylene (CTFE), hexafluoropropylene (HFP), vinylidene fluoride ($CFH=CH_2$), vinylidene difluoride (VDF), hexafluoroisobutylene (HFIB) and trifluoro-ethylene ($CF_2=CFH$), or a fluorodioxole of the general formula:

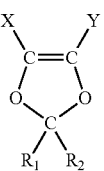

where $R_1$ and $R_2$=F or a 1-3 carbon alkyl group containing at least one fluorine, and X, Y may be F and/or H;

a fluorodioxole of the general formula:

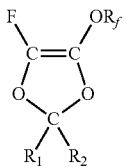

where $R_f$ is a perfluoroalkyl carbon of 1-5 atoms, and $R_1, R_2$ may be F and/or $CF_3$; or a fluorodioxalane of the general formula:

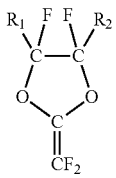

where $R_1$, $R_2$ may be F and/or a perfluoroalkyl carbon of 1-5 atoms.

The core shell TFE copolymer is produced by a polymerization process that includes placing TFE monomer and at least one comonomer in a pressurized reactor, initiating the polymerization reaction with a free radical initiator, feeding TFE monomer and comonomer into the reaction vessel during the polymerization reaction, stopping the addition of comonomer at a point in the polymerization reaction prior to completion of the polymerization reaction, and continuing the polymerization reaction by feeding only TFE monomer into the reaction vessel until the reaction is complete. It is to be appreciated that more than one comonomer may be fed into a pressurized reactor to produce multi-component copolymers, such as, for example, terpolymers.

The initial addition of TFE monomer and comonomer may be introduced into the reactor vessel as a precharge. After the polymerization reaction has started, the comonomer and TFE monomer may be sequentially added, for example, with the comonomer being added prior to the TFE monomer. Alternatively, the TFE monomer and comonomer may be simultaneously added to the reaction vessel. The TFE monomer and comonomer may be introduced incrementally or intermittently to the reaction vessel during the polymerization reaction. Higher concentrations of comonomer in the TFE copolymer produced are achieved by adding the comonomer to the reaction vessel at higher concentration levels. Comonomer may be added to the reaction vessel in an amount of at least about 1.0% by weight, at least about 2.0% by weight, at least about 3.0% by weight, at least about 3.5% by weight, at least about 4.0% by weight, at least about 4.5% by weight, or at least about 5.0% by weight. It is to be noted that the % by weight described herein with reference to the addition of the TFE monomer and/or comonomer to the reaction vessel are based upon total weight of TFE monomer and comonomer fed into the reactor vessel.

At a point between about 15% and about 90%, between about 20% and about 70%, between about 20% and about 60%, or between about 30% and about 60% of the progression of the reaction toward completion, addition of the comonomer to the reaction vessel is stopped. In at least one embodiment, the comonomer addition is stopped at about the mid-point of the polymerization reaction, e.g., at a point from about 30% to about 60% to completion. The polymerization reaction is then permitted to continue by adding only TFE monomer until the reaction is complete. Excess comonomer may be removed (e.g., evacuated) from the reactor, as needed, prior to completion of the reaction.

In the polymerization reaction, substantially non-telogenic dispersing agents may be used. Ammonium perfluoro octanoic acid (APFO or "C-8") is one non-limiting example of a suitable dispersing agent for the polymerization reaction. Programmed addition (precharge and pumping) may be utilized to add the dispersing agent to the reaction vessel. It is to be appreciated that ingredient purity is needed to achieve the desired properties in the dense articles described herein. Ionic impurities, which can increase ionic strength, in addition to soluble organic impurities, which can cause chain transfer or termination, are minimized or even eliminated. In at least one embodiment, ultra-pure water is employed.

The TFE core shell copolymer produced by the process described herein contains a core portion that includes copolymer units and a shell portion that contains substantially only TFE monomer. "Substantially only TFE monomer" as used herein is meant to denote that the shell contains (1) TFE monomer only or (2) TFE monomer and a trace amount (e.g., an unquantifiable amount) of comonomer. The TFE core shell copolymer may contain comonomer in an amount of at least about 1.0% by weight, at least about 2.0% by weight, at least about 3.0% by weight, at least about 3.5% by weight, at least about 4.0% by weight, at least about 4.5% by weight, at least about 5.0% by weight, at least about 5.5% by weight, at least about 6% by weight, at least about 7% by weight, at least about 8% by weight, at least about 9% by weight, or at least about 10% by weight. Accordingly, the amount of tetrafluoroethylene (e.g., TFE monomer) that may be present in the TFE copolymer may be less than about 99% by weight, less than about 98% by weight, less than about 97% by weight, less than about 96.5% by weight, less than about 96% by weight, less than about 95.5% by weight, or less than about 95% by weight. In some embodiments, the TFE copolymer includes at least 30% by weight TFE monomer, at least 40% by weight, at least 50% by weight, at least about 60% by weight, at least about 70% by weight, at least about 80% by weight, or at least 90% by weight. Percent by weight as it pertains to the TFE core shell copolymer is based upon the total weight of the TFE copolymer. The TFE core shell copolymer is expandable and may be expanded to produce strong, useful, expanded TFE copolymeric articles having a microstructure of nodes interconnected by fibrils.

The TFE copolymers are produced in the form of fine particles dispersed within an aqueous medium. In one embodiment, the TFE copolymer may be blended or combined, either by coagulation or dry blending with at least 5% by weight, at least about 5.5% by weight, at least about 6% by weight, at least about 6.5% by weight, at least about 7% by weight, at least about 7.5% by weight, at least about 8% by weight, at least about 8.5% by weight, at least about 9% by weight, at least about 9.5% by weight, or at least about 10% by weight of a TFE homopolymer, a thermoplastic polymer, a TFE copolymer, or combinations thereof. It is to be noted that the % by weight as used with respect to blending an additional polymer is based on the total weight of the polymer blend. Non-limiting examples of suitable thermoplastic polymers include, but are not limited to, fluorinated ethylene propylene (FEP), polyvinylidene fluoride (PVDF), perfluoro(alkyl vinyl) ethers (PAVE), perfluoroelastomeric materials (FFKM), a polymer of tetrafluoroethylene, hexafluoropropylene, and vinylidene fluoride (THV), perfluoroalkoxy alkane (PFA), a copolymer of ethylene and tetrafluoroethylene (ETFE), and polychlorotrifluoroethene (PCTFE). The type and/or amount of the polymer(s) to be blended may be selected to provided desirable mechanical or functional end properties.

The TFE copolymers may be processed into a TFE copolymer film utilizing conventional techniques, such as, for example, those identified in U.S. Pat. No. 3,953,566 to Gore. For instance, the TFE copolymer may be subjected to a ram extrusion process where the TFE copolymer is combined with a suitable lubricant (e.g., Isopar® K), blended, compressed into a pellet, and extruded through a die to form a tape. The direction of extrusion is referred to as the y-direction or longitudinal direction. The resulting tape is then dried to remove or substantially remove the lubricant. The term "lubricant", as used herein, is meant to describe a processing aid that includes, and in some embodiments, consists of, an incompressible fluid that is not a solvent for the polymer at processing conditions. Additionally, the fluid-polymer surface interactions are such that it is possible to create an homogenous mixture. The phrase "substantially remove the lubricant" is meant to denote that the lubricant is nearly or completely removed from the TFE copolymer tape.

The dried TFE copolymer tape may then be expanded in at least one direction to form a TFE copolymer film. The TFE copolymer film possess at least three separate endotherms. A first endotherm occurs below about 300° C. In at least one embodiment, a first endotherm occurs between about 50° C. and about 300° C. A second endotherm occurs between about 320° C. and about 350° C. A third endotherm in the dense TFE copolymer film and dense article occurs from about 350° C. to about 400° C. In exemplary embodiments, the third endotherm occurs at about 380° C. It is to be understood that the terms "first", "second", and "third" as used herein are not representative of any kind of order, but are used rather to differentiate the existence of three separate and distinct endotherms in the TFE copolymer film. Also, it is to be noted that blends can be made with the TFE core shell copolymer by blending with another TFE homopolymer, a thermoplastic polymer, and/or another TFE copolymer, such as described herein, which may create an additional endotherm.

In at least one embodiment, the tape is simultaneously expanded in the longitudinal and transverse directions (e.g., both the x- and y-directions) to form the TFE copolymer film. The expansion in the longitudinal (y-direction) may occur at a stretch rate of about 10%/sec or lower, about 1,000%/sec or higher, or between about 10%/second to about 1,000%/sec. The expansion in the transverse (x-direction) may occur at a stretch rate of about 10%/sec or lower, about 1,000%/sec or higher, or between about 10%/second to about 1,000%/sec. It is to be appreciated that the expansion of the TFE copolymer tape may be conducted in either the x- or y-direction or both the x-, y-directions, either sequentially or simultaneously, utilizing a pantograph machine or continuously in a tenter frame or similar machine. Suitable expansion ratios may vary significantly, such as from 1:1 to 1:1,000 or from 1:1 to 1:10,000 or greater and at varying expansion rates.

The TFE copolymer film is then compressed in a direction normal to the x-y plane to form a densified TFE copolymer film and to achieve a reduction in porosity. One compression process that may be utilized to densify the TFE copolymer film is described in U.S. Pat. No. 5,374,473 to Knox, et al.

For example, the TFE copolymer film may be densified by positioning the TFE copolymer film between two plates that can withstand heat and pressure, placing the plates into a suitable autoclave bag (e.g., bag made of polyimide film), and then drawing a vacuum inside the bag while gradually raising the temperature and pressure over a period of time. It is to be appreciated that such an autoclave process may be replaced with a platen press that has been equipped with a vacuum enclosure allowing evacuation of air and gasses from the TFE copolymer film.

Alternatively, the TFE copolymer film may be compressed without being placed under vacuum on an appropriate batch press, such as a platen press, or alternatively in a continuous manner by compressing between rollers or other suitable compression equipment at a linear speed and at a pressure and temperature to substantially eliminate the pores. It is to be appreciated that the TFE copolymer film may be compressed, with or without vacuum, and with or without the application of heat (e.g., compression conducted at or about room temperature).

In addition, the TFE copolymer film may be compressed (e.g., densified) at a temperature up to about 400° C. In one exemplary embodiment, the TFE copolymer film is compressed at a temperature below the first endotherm, e.g., at a temperature below about 300° C., to form the dense TEE copolymer film. In another embodiment, the TFE copolymer film is densified at a temperature above the first endotherm, e.g., at a temperature above about 300° C. In yet another embodiment, the TFE copolymer film is compressed at a temperature above the second endotherm, e.g., at a temperature above about 320° C. In a further embodiment, the TFE copolymer film is densified at a temperature above the first endotherm and below the second endotherm, e.g., at a temperature between about 300° C. and 350° C. In yet another embodiment, the TFE copolymer film is densified at a temperature between the second endotherm and the third endotherm, e.g., at a temperature from about 320° C. to about 400° C. It is to be appreciated that a heat treatment at any of these temperatures may occur prior to and/or after compressing the TFE copolymer film.

The TFE copolymer film may optionally be heated to the densification temperature (e.g., pre-heated and/or post-heated) prior to and/or after compressing the TFE copolymer film to form a dense TFE copolymer film (e.g., a dense article). In one embodiment, the process ends here with the formation of a dense article, i.e., a TFE copolymer film that has been compressed into a dense TFE copolymer film.

In a further embodiment, the process continues and the dense TFE copolymer film is then stretched or deformed at a suitable rate and temperature in at least one direction to form a dense article, i.e., a TFE copolymer film that has been compressed and subsequently stretched into a dense article. Thus, in at least one embodiment, the dense TFE copolymer film is stretched to form a dense article. As used herein, the term "dense" is meant to describe a dense article that possesses a void volume less than about 20%. The dense articles may possess a void volume less than about 20%, less than about 15%, less than about 10%, less than about 8%, less than about 5%, less than about 3%, or less than about 1%. Additionally, the dense articles are thin, and may have a thickness less than about 250 microns, less than about 150 microns, less than about 100 microns, less than about 50 microns, less than about 30 microns, less than about 10 microns, less than about 5 microns, or less than about 1 micron. It is to be understood that each of the dense articles described herein are formed from TFE copolymer films including core shell TFE copolymers and may be used in similar or identical applications.

In one or more exemplary embodiment, the dense TFE copolymer film is stretched in the longitudinal and transverse directions (e.g., both the x- and y-directions). The deformation in the longitudinal (y-direction) may occur at a stretch rate of about 10%/sec or lower, about 1,000%/sec or higher, or between about 10%/second to about 1,000%/sec. The deformation in the transverse (x-direction) may occur at a stretch rate of about 10%/sec or lower, about 1,000%/sec or higher, or between about 10%/second to about 1,000%/sec. It is to be appreciated that the stretching may be conducted in either the x- or y-direction or both the x-, y-directions, either sequentially or simultaneously, utilizing a pantograph machine or continuously in a tenter frame or similar machine.

Additionally, the dense TFE copolymer film may be stretched or deformed at a temperature at or above the first endotherm, e.g., at a temperature at or above about 300° C. In another embodiment, the dense TFE copolymer film is stretched at a temperature at or above the second endotherm, e.g., at a temperature at or above about 320° C. In a further embodiment, the dense TFE copolymer film is stretched at a temperature above the first endotherm and below the second endotherm, e.g., at a temperature between about 300° C. and 350° C. In a further embodiment, the dense TFE copolymer film is stretched at a temperature between the second endotherm and the third endotherm, e.g., at a temperature from about 320° C. to about 400° C. The densified TFE copolymer film may be stretched at a rate of about 10%/sec or lower, about 1,000%/sec or higher, or between about 10%/second to about 1,000%/sec. The stretching results in a reduction in unit weight and thickness. It is to be appreciated that a heat treatment at any of these temperatures may occur prior to and/or after stretching the dense TFE copolymer film.

The dense articles may be utilized as barrier materials. The TFE copolymer films in the dense articles exhibit a methane permeability of less than about 20 µg*micron/cm$^2$/min, less than about 15 µg*micron/cm$^2$/min, less than about 10 µg*micron/cm$^2$/min, less than about 5 µg*micron/cm$^2$/min, less than about 1.0 µg*micron/cm$^2$/min, or less than about 0.5 µg*micron/cm$^2$/min. Further, the dense article has a matrix tensile strength in at least one direction that is greater than or equal to about 5,000 psi, greater than or equal to about 25,000 psi, greater than or equal to about 50,000 psi, greater than or equal to about 75,000 psi or greater than or equal to about 100,000 psi, or higher.

In addition, the dense articles exhibit adhesion characteristics that cannot be achieved in conventional polytetrafluoroethylene (PTFE) homopolymers. That is, the dense TFE copolymer film and dense article can be adhered to itself or to other materials after subjecting it to lower temperature and/or shorter time and/or lower pressure than what is required for adhering PTFE homopolymer to itself or to other substrates, such as, for example, adhesion promoting substrates, polymeric substrates, or metal substrates. Such adhesion characteristics enable barrier materials to be formed without the need to adhere other substrates, which per unit volume, possess less barrier and mechanical performance. As a result, barrier properties associated with the dense TFE copolymer films and dense article are maximized.

The TFE copolymer film, the dense TFE copolymer film, and the dense article may be laminated, adhered, or otherwise bonded (e.g., thermally, mechanically, or chemically) to a substrate. Non-limiting examples of suitable substrates include, but are not limited to, fluorinated ethylene propylene (FEP), perfluoroalkoxy alkane (PFA), polytetrafluoroethylene (PTFE), a polymer of tetrafluoroethylene, hexafluoropropylene, and vinylidene fluoride (THV), polyurethanes, polyamides, ethylene vinyl alcohol (EVOH), and polyvinyl chloride (PVC). The substrate may also be a metallic sheet, an inorganic sheet, or pressure sensitive adhesive. Such laminated structures may facilitate or enhance further bonding to additional layers, such as textiles.

TEST METHODS

It should be understood that although certain methods and equipment are described below, other methods or equipment determined suitable by one of ordinary skill in the art may be alternatively utilized.

Differential Scanning calorimetry (DSC)

This test was performed using a TA Instruments Q2000 DSC and TA Instruments standard aluminum pans and lids for Differential Scanning calorimetry (DSC). Weight measurements were performed on a Sartorius MC 210P microbalance. All spectra had endotherms reported in the positive direction on the y-axis.

Calibration of the Q2000 was performed by utilizing the Calibration Wizard available through the Thermal Advantage software supplied with the device. All calibration and resulting scans were performed under a constant nitrogen flow of 50 ml/min.

The sample was loaded into the pan and the weight was recorded to 0.01 mg precision, with samples ranging from 5.00 mg to 10.00 mg. These values were entered into the Thermal Advantage control software for the Q2000. The lid was placed on the pan and crimped using a standard press. A similar pan for reference was prepared, with the exception of the sample article, and its weight was also entered into the software. The pan containing the sample article was loaded onto the sample sensor in the Q2000 and the empty pan was loaded onto the reference sensor. The samples were then equilibrated at −50° C. and ramped at 10° C./min to 410° C. Data were analyzed using Universal Analysis 2000 from TA Instruments.

Methane Permeability

Standard Procedure:

The apparatus used to measure methane permeation comprised of a stainless steel test cell with a top half, a bottom half, an inlet for methane gas, and an inlet for zero air. The term "zero air" refers to compressed air passing through a catalyst bed to remove any hydrocarbons in the air so that the methane is the only hydrocarbon the FID detector measures. The bottom half of the test cell was first purged with zero air. The testing film is sandwiched between the two halves and sealed. A tight seal is formed by two o-rings.

Methane gas and zero air were then introduced into the test sample by way of the inlets. The flow of the methane gas and zero air were controlled using a needle valve and a mass flow controller (Model No. Brooks 5850E), respectively. Methane gas came in from the bottom inlet and came out through the bottom exhaust outlet, which ensured that there is no back pressure on the test sample.

The methane gas which permeated through the test sample was carried in zero air and fed in to the FID detector (Model 8800B, Baseline-Mocon, Inc.). The FID detector continuously measured the concentration of the methane gas, which permeated through the test sample. The detector was connected to a data acquisition system to acquire voltage signals which were then converted to methane concentration ($C_{methane}$) values using a known three point calibration curve.

The test duration lasted at least until the methane concentration reached a steady state. The test duration typically ranged from about 15 minutes to about 40 minutes. The average of the data ($C_{methane}$) collected during the last two minutes of the test duration was reported.

The methane flux (in units of g/cm²/min) was calculated by the following equation:

$$\text{Methane flux} = 0.000654 * C_{methane} * R/A$$

wherein $C_{methane}$ is the average methane concentration in ppm, R is the flow rate of zero air in cm³/min, and A is the area of the test sample in cm². Methane permeation was measured in duplicate and the average value of methane flux based on two samples was reported.

Accumulation Procedure:

In this procedure, the following variation to the above described standard procedure was used. The zero air inlet and the port were closed while the methane gas was introduced into the test sample. Without zero air flow into the top half of the test cell, the methane gas which permeated through the test sample accumulated inside the top half of the cell. After a fixed duration of methane gas accumulation (typically about 30 minutes to about 60 minutes), the zero air inlet and the port were opened, the methane gas accumulated was then carried in zero air to the FID detector, which measured the concentration of the methane gas ($C_{methane}$) accumulated in the cell during the testing duration. The above equation was used to calculate the methane flux.

Void Percent (%)

Void (%) of the sample was estimated by the difference between bulk density ($\rho_{bulk}$) and skeletal density ($\rho_{skeleton}$) of the sample. The test sample was die-cut into coupons shaped into a circle with a diameter of about 20.3 mm. Four coupons were cut from different locations of the test sample. The thickness was measured at four different locations of each coupon by using the Mitutoyo Litematic VL-50A contact gauge. The average value of thickness was calculated for each coupon. The thickness of the test sample was reported based on the average value for the four coupons. The weight of each coupon was measured using a microbalance (Mettler Toledo Model AT20). The weight of the test sample was reported based on the average value for the four coupons.

The bulk density ($\rho_{bulk}$) was then computed by dividing the weight of the test sample by the product of test sample area and test sample thickness. The coefficient of variance (CV) for the bulk density measurement was typically less than 5% with a mean CV of about 3.6%.

Skeletal density ($\rho_{skeleton}$) or the true density of the test sample was measured using a standard helium pycnometer (Model AccuPyc 1340 with a sample cup of 1 cm³ in volume). The test sample mass was kept above 0.2 g, which was the minimum weight required to get within 99% of the skeletal density value. The instrument was first calibrated using a steel ball with a known volume of 0.05656 cm³. The following test conditions were used; purge cycles=20, purge fill pressure and cycle fill pressure=19.5 psig. An average of 20 measurements of the test same sample were reported. The coefficient of variance (CV) of the 20 replicates was less than 0.2%.

The void percent (%) was then calculated using the following equation;

$$\text{Void \%} = (\rho_{skeleton} - \rho_{bulk})/\rho_{skeleton} * 100$$

Tensile Break Load Measurements & Matrix Tensile Strength (MTS)

Tensile break load was measured using an Instron® 1122 tensile test machine equipped with flat-faced grips and a 0.445 kN load cell. The gauge length was 2.54 cm and the cross-head speed was 2.54 cm/min. The test sample dimensions were 7.6 cm by 0.64 cm. For longitudinal MTS measurements, the larger dimension of the sample was oriented in the machine direction. For the transverse MTS measurements, the larger dimension of the sample was oriented perpendicular to the machine direction. Each sample was weighed using a scale (Mettler Toledo Model AG204). The samples were then tested individually on the tensile tester. Three different samples from each direction were measured. The average of the three maximum load (i.e., the peak force) measurements was used. The longitudinal and transverse MTS were calculated using the following equation:

$$\text{MTS} = (\text{maximum load/cross-section area}) * (\text{intrinsic density of PTFE})/\text{intrinsic density of the test sample};$$

where the bulk density of the inventive copolymer film is taken to be equivalent the intrinsic density of PTFE is taken to be 2.2 g/cc.

EXAMPLES

Example 1

To a 50-liter, horizontal polymerization reactor equipped with a 3-bladed agitator was added 1.5 kg wax, 28 kg of deionized (DI) water, 18 g of ammonium perfluorooctanoic acid (APFO), and 5 g of succinic acid dissolved in 50 g of DI water. The reactor and contents were heated above the melting point of the wax. The reactor was repeatedly evacuated and pressurized (to about 1 Atm or less) with TFE until the oxygen level was reduced to 20 ppm or less. The contents were briefly agitated at 60 rpm between evacuation and purge cycles to ensure that the water was deoxygenated.

The reactor was heated to 83° C. and agitated at 60 rpm. Subsequently, 2.0 Mpa of VDF was added, followed by addition of TFE until the pressure reached 2.8 Mpa. At this time, $KMnO_4$ in a DI water solution (0.2 g/L) was injected at 80 mL/min until approximately 1 kg of TFE was added. The $KMnO_4$ was added at 60 mL/min for the next 2 kg of TFE. The $KMnO_4$ was then added at 80 mL/min until 4 kg more of TFE was consumed. The total amount of $KMnO_4$ solution added was 4.61 kg.

Approximately 320 g of 20% APFO solution was added in 40 ml increments, the first increment being added after about 1 kg of TFE had been added, followed by increments after each additional 0.5 kg of TFE for the next 2 kg of TFE and then additions for the next 3 kg of TFE, so that the final increment was added after 8 kg of TFE had been reacted.

VDF and TFE were added after the first added 1 kg of TFE was consumed. VDF and TFE were then added sequentially such that for each 0.5 kg of consumed TFE was followed by 0.5 kg of VDF until 2 kg of TFE and 2 kg of VDF were consumed. The polymerization continued by only feeding TFE until the end of the polymerization.

The polymerization reaction stopped after 14 kg of TFE had been added to the reactor. The weight of the dispersion produced was 48.90 kg containing 33.21% solids. The dispersion was coagulated with nitric acid and dried at 130° C.

The raw dispersion particle size (RDPS) of the polymer particle was 0.321 microns. The VDF concentration in the copolymer was determined to be 27.9 mol % (19.9 wt %), as measured by nuclear magnetic resonance (NMR) spectroscopy.

A dense article using the above described fine powder resin including the core shell copolymer of TFE and VDF was prepared as follows. The resin was mixed with Isopar® K (Exxon Mobil Corp., Fairfax, Va.) at a concentration of 0.201 g/g of resin and formed into a pellet approximately 10.2 cm in diameter at a pressure of 2758 kPa. The pellet was heated to 49° C. and ram extruded into a tape having dimensions of 0.064 cm in thickness and 20.32 cm in width, through a die which affected a reduction ratio of 63 to 1, at an average extrusion pressure of 72678 kPa. The reduction ratio is the ratio of the cross sectional area of the extruder barrel to the cross sectional area of the extruded tape. The tape was dried by heating at 130° C. in order to remove the lubricant. The width of the dried tape was 19.05 cm.

Using a pantograph machine, the tape was heated at 200° C. for 120 seconds and then expanded in the longitudinal and transverse directions simultaneously at a ratio of 2.7:1 in the longitudinal direction and 2.9:1 in the transverse direction while maintaining a temperature of about 200° C. The average engineering strain rate was calculated to be about 700%/second.

The resulting expanded TFE copolymer film was densified as follows. One ply of the expanded TFE-VDF copolymer film with a nominal thickness of 312 microns was placed between two caul plates in an autoclave bag assembled from polyimide film (Kapton® commercially available from DuPont deNemours, Wilmington, Del.). The assembly was placed in an autoclave (Vacuum Press International Model Econoclave® 2X4, commercially available from ASC Process Systems), vacuum was drawn in the bag and the pressure and temperature of the autoclave were gradually raised based upon the temperature and pressure conditions summarized in FIG. 1.

The resulting densified TFE-VDF copolymer film was approximately 62.4 microns thick. The densified TFE-VDF copolymer film was then placed in a pantograph machine where the sheet was heated to a temperature of 370° C. for a period of 90 seconds. The densified TFE-VDF copolymer film, while still heated, was then stretched in the longitudinal direction and transverse direction at a ratio of 2.5:1 and 1.3:1, respectively at a rate of 100%/sec.

The resultant dense article was characterized and the results are given in Table 1. The standard procedure described above under Methane Permeability was used to measure methane permeation.

Figure 2:
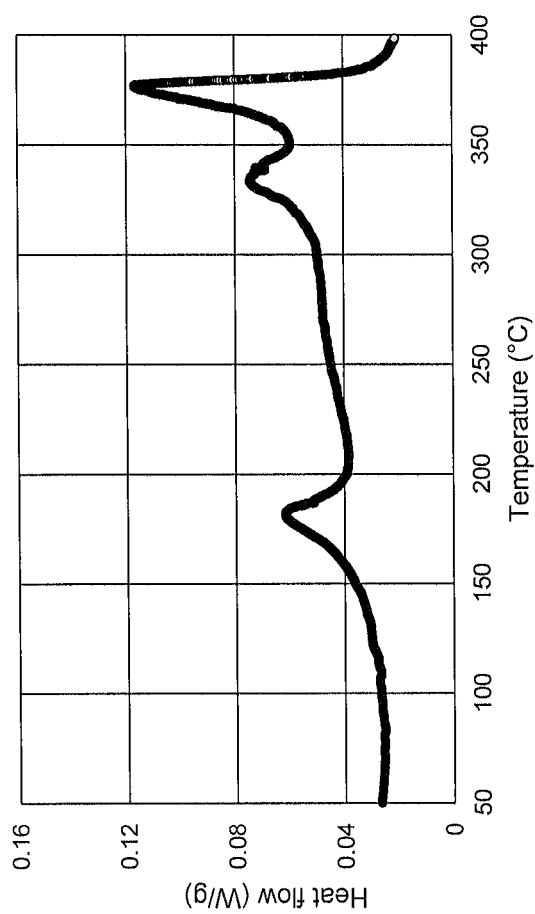
FIG. 2 is a differential scanning calorimetry scan (DSC) depicting three endotherm peaks for a TFE-VDF dense article according to at least one embodiment of the invention.

FIG. 2 depicts a differential scanning calorimetry (DSC) scan showing the melt transition temperature peaks of the dense article, clearly indicating the presence of three peaks, the first peak at 177.73 C, the second peak at 341.83° C., and the third peak at 369.19° C.

Example 2

To a 50 liter, horizontal polymerization reactor equipped with a 3-bladed agitator was added 1.5 kg wax, 28 kg of deionized (DI) water, 18 g of ammonium perfluorooctanoate (APFO), and 5 g of succinic acid dissolved in 50 g of DI water. The reactor and contents were heated above the melting point of the wax. The reactor was repeatedly evacuated and pressurized (to 1 Atm or less) with TFE until the oxygen level was reduced to 20 ppm or less. The contents were briefly agitated at 60 rpm between evacuation and purge cycles to ensure that the water was deoxygenated. The reactor was heated to 83° C. and agitated at 60 rpm. Subsequently, 2.8 Mpa of TFE was added followed by addition of $KMnO_4$ in a DI water solution (0.6 g/L) which was injected at 3.75 mL/min until approximately 1 kg of TFE added.

The $KMnO_4$ solution was added at 4.6 mL/min for the next 1 kg of TFE. The $KMnO_4$ solution was then added at 50 mL/min until 1 kg more of TFE was consumed. The $KMnO_4$ solution was then added at 30 mL/min until 1 kg more of TFE was consumed. The $KMnO_4$ solution was then added at 40 mL/min until 1 kg more of TFE was consumed. The $KMnO_4$ solution was then added at 50 mL/min until 1 kg more of TFE was consumed. The $KMnO_4$ solution was then added at 25 mL/min until 1 kg more of TFE was consumed. The $KMnO_4$ solution was then added at 2 mL/min until 1 kg more of TFE was consumed. The total amount of $KMnO_4$ solution added was 5.725 kg.

Approximately 320 g of 20% APFO solution was added in 40 mL increments, the first increment being added after about 1 kg of TFE was consumed, followed by increments after each additional 1 kg of TFE for the next 6 kg of TFE, so that the final increment was added after 7 kg of TFE had been reacted.

CTFE was pumped into the reactor via liquid feed using a syringe pump. CTFE and TFE were added after the first added 1 kg of TFE was consumed. CTFE and TFE were then added continuously such that for each 1 kg of consumed TFE there was 0.8 L of CTFE consumed. This continued until a total of 3 kg of TFE was consumed and 1.6 L of CTFE was consumed. The polymerization continued by only feeding TFE until the end of the polymerization.

The polymerization reaction stopped after 14.1 kg of TFE had been added to the reactor. The weight of the dispersion produced was 51.78 kg containing 35.61% solids. The dispersion was coagulated with nitric acid and dried at 130° C.

The raw dispersion particle size (RDPS) of the polymer particle was 0.266 microns. The CTFE concentration in the copolymer was measured to be 13 mol % (15 wt %), as measured by nuclear magnetic resonance (NMR) spectroscopy.

A dense article using the above described fine powder resin including the copolymer of TFE and CTFE was prepared as follows. The resin was mixed with Isopar® K (Exxon Mobil Corp., Fairfax, Va.) at a concentration of 0.252 g/g of resin and formed into a pellet approximately 10.2 cm in diameter at a pressure of 2758 kPa. The pellet was heated to 49° C. and ram extruded into a tape having dimensions of 0.051 cm in thickness and about 20.32 cm in width, through a die which affected a reduction ratio of 79 to 1, at an average extrusion pressure of 36804 kPa. The reduction ratio is the ratio of the cross sectional area of the extruder barrel to the cross sectional area of the extruded tape. The tape was dried by heating at 180° C. in order to remove the lubricant. The width of the dried tape was 18.1 cm.

Using a pantograph machine, the tape was heated at 250° C. for 120 seconds and then expanded in the longitudinal and transverse directions simultaneously at a ratio of 2.7:1 in the longitudinal direction and 2.9:1 in the transverse direction while maintaining a temperature of about 250° C. The average engineering strain rate was calculated to be about 700%/second.

Figure 3:
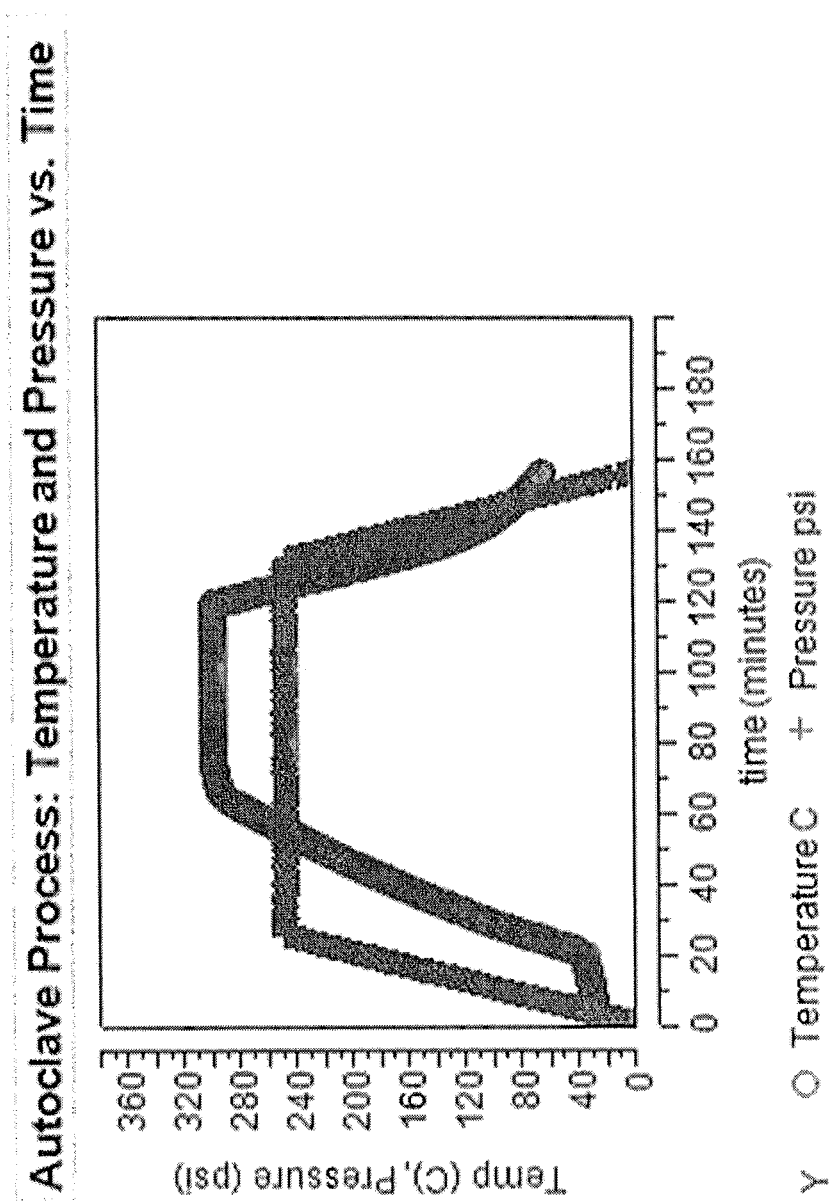
FIG. 3 is a graphical illustration of temperature and pressure vs. time for an autoclave process used in densifying a TFE-CTFE copolymer according to at least one embodiment of the invention.

The resulting expanded TFE-CTFE copolymer film was densified as follows. One ply of the expanded TFE-CTFE copolymer film with a nominal thickness of 233.4 micron was placed between two caul plates in an autoclave bag assembled from polyimide film (Kapton® commercially available from DuPont deNemours, Wilmington, Del.). The assembly was placed in an autoclave (Vacuum Press International Model Econoclave® 2X4, commercially available from ASC Process Systems), vacuum was drawn in the bag and the pressure and temperature of the autoclave were gradually raised based upon the temperature and pressure conditions summarized in FIG. 3. The resulting densified TFE-CTFE copolymer film was approximately 46.7 microns thick. The densified TFE-CTFE copolymer film was then placed in a pantograph machine wherein the densified TFE copolymer film was heated to a temperature of 370° C. for a period of 45 seconds. The densified TFE-CTFE copolymer film, while still heated, was then stretched in the longitudinal direction and transverse direction at a ratio of 2.5:1 and 1.3:1, respectively and a stretch rate of 100%/sec.

The resultant dense article was characterized and the results are given in Table 1. The standard procedure described above under Methane Permeability was used to measure methane permeation.

Figure 4:
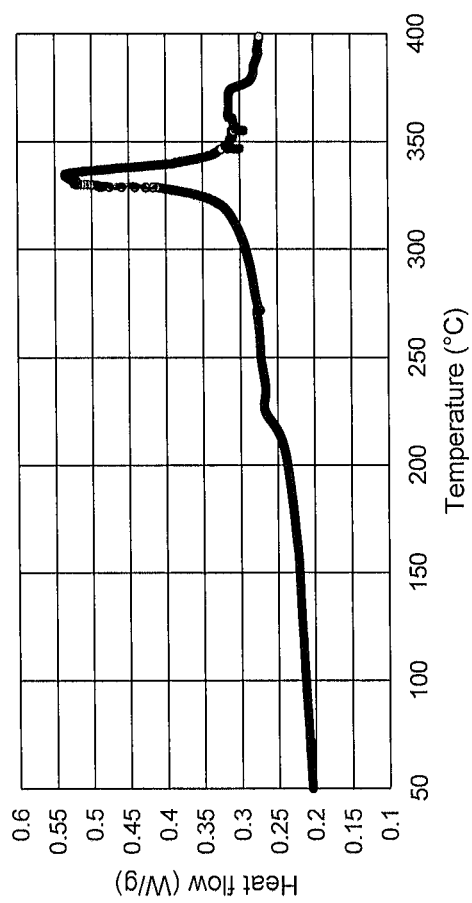
FIG. 4 is a differential scanning calorimetry scan (DSC) depicting three endotherm peaks for a TFE-CTFE dense article according to another embodiment of the invention.

FIG. 4 depicts a differential scanning calorimetry (DSC) scan showing the melt transition temperature peaks of the dense article, clearly indicating the presence of three peaks, the first peak at 225.47° C., the second peak at 334.23° C., and the third peak at 373.82° C.

Example 3

A dense article using the fine powder resin of Example 1 was prepared as follows. The resin was mixed with Isopar® K (Exxon Mobil Corp., Fairfax, Va.) at a concentration of 0.201 g/g of resin and formed into a pellet approximately 10.2 cm in diameter at a pressure of 2758 kPa. The pellet was heated to 49° C. and ram extruded into a tape having dimensions of 0.064 cm in thickness and 20.32 cm in width, through a die which affected a reduction ratio of 63 to 1, at an average extrusion pressure of 72678 kPa. The reduction ratio is the ratio of the cross sectional area of the extruder barrel to the cross sectional area of the extruded tape. The tape was dried by heating at 130° C. in order to remove the lubricant. The width of the dried tape was 19.05 cm.

Using a pantograph machine, the tape was heated at 200° C. for 120 seconds and then expanded in the longitudinal and transverse directions simultaneously at a ratio of 3:1 in the longitudinal direction and 4.9:1 in the transverse direction while maintaining a temperature of about 200° C. The average engineering strain rate was calculated to be about 700%/second.

The resulting expanded TFE-VDF copolymer film was densified as follows. One ply of the membrane with a nominal thickness of 181.0 micron was placed between two caul plates in an autoclave bag assembled from polyimide film (Kapton® commercially available from DuPont deNemours, Wilmington, Del.). The assembly was placed in an autoclave (Vacuum Press International Model Econoclave® 2X4, commercially available from ASC Process Systems), vacuum was drawn in the bag, and the pressure and temperature of the autoclave were gradually raised based upon the temperature and pressure conditions summarized in FIG. 3. The resulting densified TFE-VDF copolymer film was approximately 36.2 microns thick.

The densified TFE-VDF copolymer film was characterized and the results are given in Table 1. The accumulation procedure described above under Methane Permeability was used to measure methane permeation.

Figure 5:
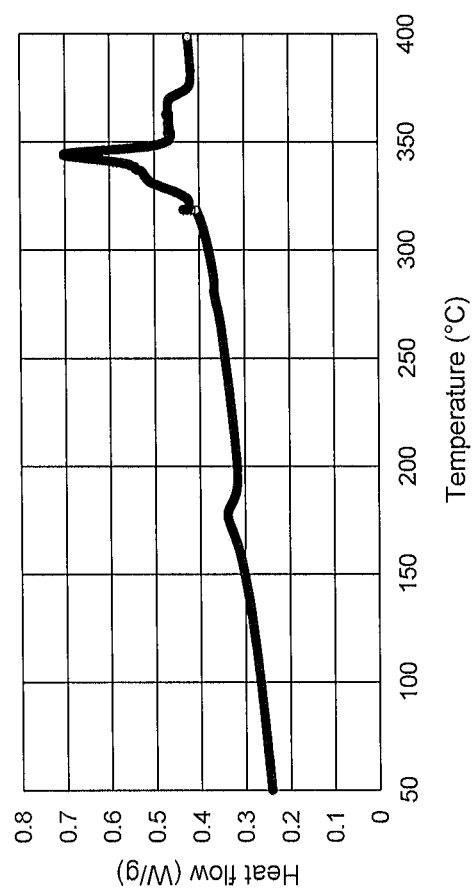
FIG. 5 is a differential scanning calorimetry scan (DSC) depicting three endotherm peaks for a dense TFE-VDF copolymer film according to an embodiment of the invention.

FIG. 5 includes differential scanning calorimetry (DSC) scans showing the melt transition temperature peaks of the densified TFE copolymer film, clearly indicating the presence of three peaks, the first peak at 176.51° C., the second peak at 343.87° C., and the third peak at 369.2° C.

Example 4

A dense article using the fine powder resin of Example 2 was prepared as follows. The resin was mixed with Isopar® K (Exxon Mobil Corp., Fairfax, Va.) at a concentration of 0.252 g/g of resin and formed into a pellet approximately 10.2 cm in diameter at a pressure of 2758 kPa. The pellet was heated to 49° C. and ram extruded into a tape having dimensions of 0.051 cm in thickness and 20.32 cm in width, through a die which affected a reduction ratio of 79 to 1, at an average extrusion pressure of 36804 kPa. The reduction ratio is the ratio of the cross sectional area of the extruder barrel to the cross sectional area of the extruded tape. The tape was dried by heating at 180° C. in order to remove the lubricant. The width of the dried tape was 18.1 cm.

Using a pantograph machine, the tape was heated at 250° C. for 120 seconds and then expanded in the longitudinal and transverse directions simultaneously at a ratio of 2.8:1 in the longitudinal direction and 4.5:1 in the transverse direction while maintaining a temperature of about 250° C. The average engineering strain rate was calculated to be about 700%/second.

The resulting expanded TFE-CTFE copolymer film was densified as follows. One ply of the expanded TFE-CTFE copolymer film with a nominal thickness of 155.0 microns was placed between two caul plates in an autoclave bag assembled from polyimide film (Kapton® commercially available from DuPont deNemours, Wilmington, Del.). The assembly was placed in an autoclave (Vacuum Press International Model Econoclave® 2X4, commercially available from ASC Process Systems), vacuum was drawn in the bag and the pressure and temperature of the autoclave were gradually raised based upon the temperature and pressure conditions summarized in FIG. 3. The resulting densified TFE-CTFE copolymer film was approximately 31.0 microns thick.

The densified TFE-CTFE copolymer was characterized and the results are given in Table 1. The accumulation procedure described above under Methane Permeability was used to measure methane permeation.

Figure 6:
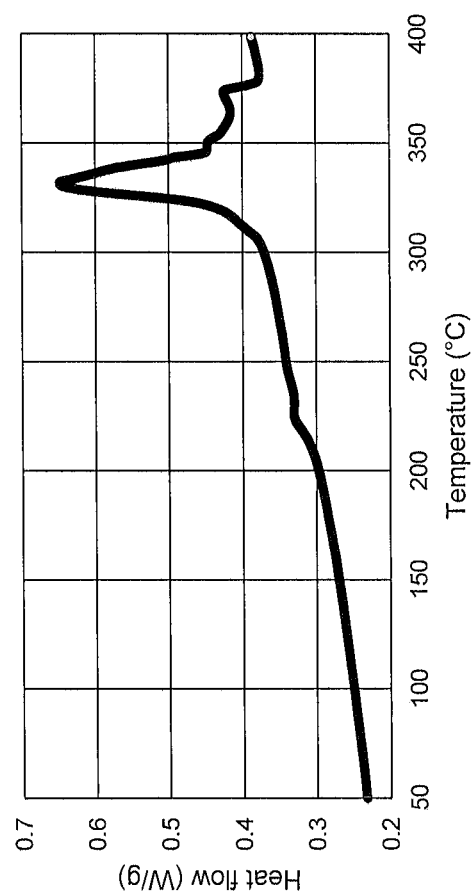
FIG. 6 is a differential scanning calorimetry scan (DSC) depicting three endotherm peaks for a dense TFE-CTFE copolymer film according to at least one embodiment of the invention.

FIG. 6 depicts a differential scanning calorimetry (DSC) scan showing the melt transition temperature peaks of the densified TFE-CTFE copolymer, clearly indicating the presence of three peaks, the first peak at 223.86° C., the second peak at 331.21° C. and the third peak at 373.64° C.

Comparative Example

A dense article using the fine powder resin comprising only PTFE (Product 601A, DuPont deNemours, Wilmington, Del.) was prepared as follows. The resin was mixed with Isopar® K (Exxon Mobil Corp., Fairfax, Va.) at a concentration of 0.151 g/g of resin and formed into a pellet approximately 10.2 cm in diameter at a pressure of 2758 kPa. The pellet was heated to 49° C. and ram extruded into a tape having dimensions of 0.064 cm in thickness and 20.32 cm in width, through a die which affected a reduction ratio of 63 to 1, at an average extrusion pressure of 74463 kPa. The reduction ratio is the ratio of the cross sectional area of the extruder barrel to the cross sectional area of the extruded tape. The tape was dried by heating at 130° C. in order to remove the lubricant. The width of the dried tape was 19.05 cm.

Using a pantograph machine, the tape was heated at 300° C. for 120 seconds and then expanded in the longitudinal and transverse directions simultaneously at a ratio of 2.6:1 in the longitudinal direction and 2.8:1 in the transverse direction while maintaining a temperature of about 300° C. The average engineering strain rate was calculated to be about 100%/second.

Figure 7:
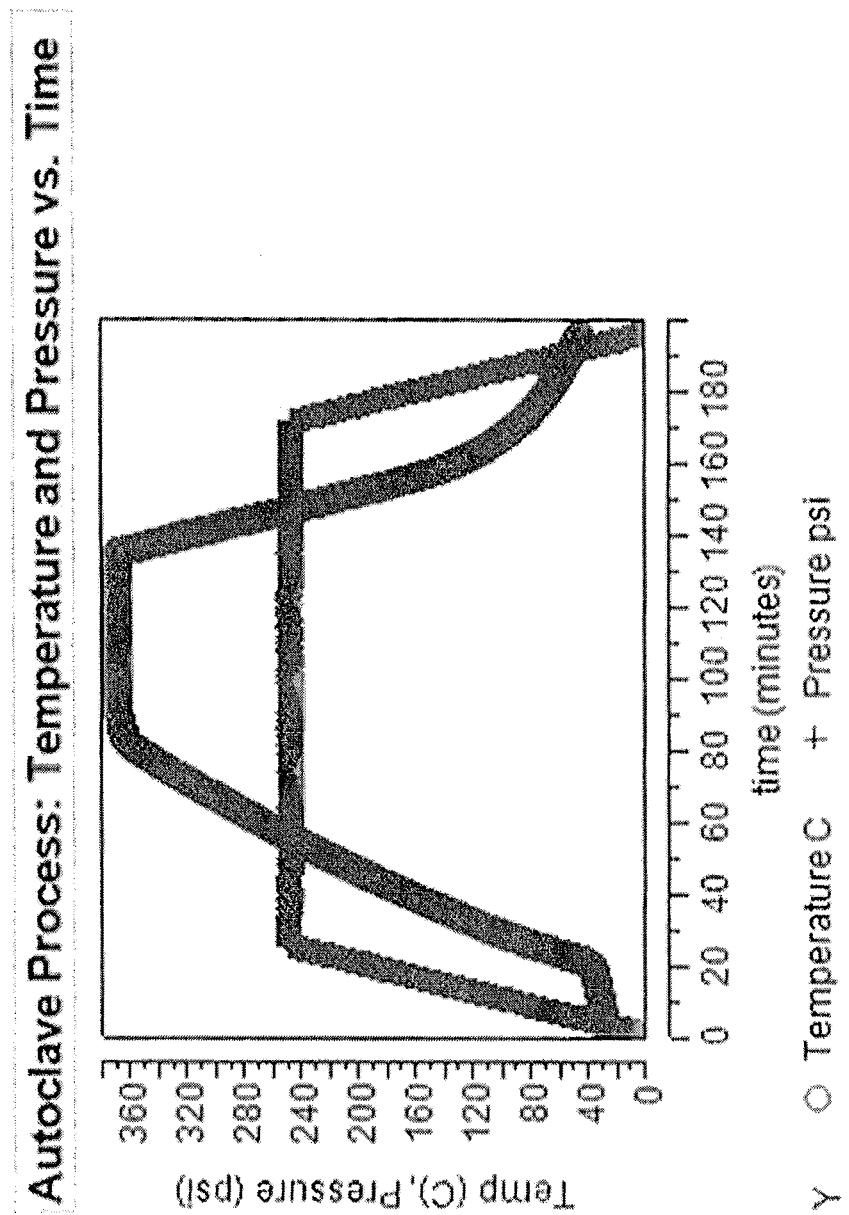
FIG. 7 is a graphical illustration of temperature and pressure vs. time for an autoclave process used in densifying a conventional PTFE homopolymer.

The resulting expanded PTFE membrane was densified as follows. One ply of the expanded PTFE membrane with a nominal thickness of 381.4 micron was placed between two caul plates in an autoclave bag assembled from polyimide film (Kapton® commercially available from DuPont deNemours, Wilmington, Del.). The assembly was placed in an autoclave (Vacuum Press International Model Econoclave® 2X4, commercially available from ASC Process Systems), vacuum was drawn in the bag, and the pressure and temperature of the autoclave were gradually raised based upon the temperature and pressure conditions summarized in FIG. 7. The resulting compressed ePTFE membrane was approximately 76.3 microns thick. The compressed ePTFE membrane was then placed in a pantograph machine where the compressed ePTFE membrane was heated to a temperature of 370° C. for a period of 240 seconds. The compressed ePTFE membrane, while still heated, was then stretched in the longitudinal direction and transverse direction at a ratio of 2.95:1 and 1.5:1, respectively, at a rate of 5%/sec to form a dense PTFE article.

The resultant dense article was characterized and the results are given in Table 1. The standard procedure described above under the Methane Permeability was used to measure methane permeation.

Figure 8:
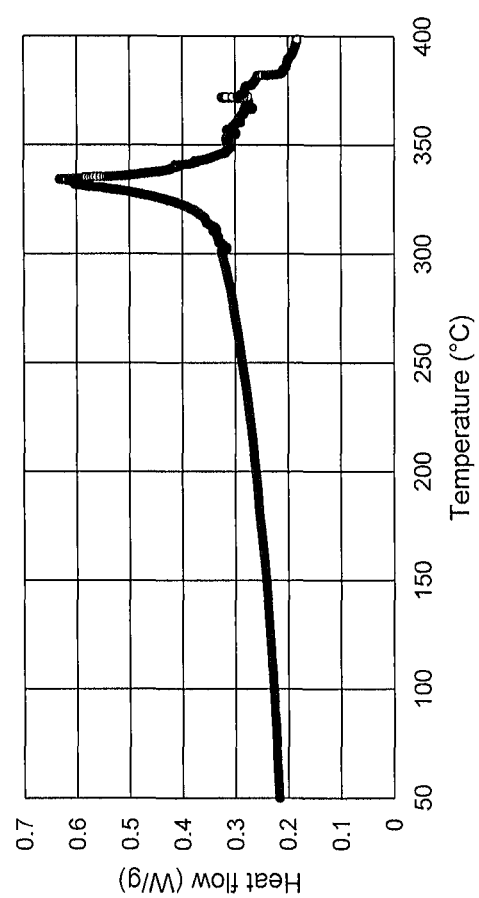
FIG. 8 is a differential scanning calorimetry scan (DSC) depicting two endotherm peaks for a dense PTFE article.

FIG. 8 depicts a differential scanning calorimetry (DSC) scan showing the melt transition temperature peaks of the dense PTFE article, the first peak at 334.11° C. and the second peak at 371.96° C.

TABLE 1

| | Thickess (micron) | Methane Permeability normalized to thickness (μg*micron/cm²/min) | Void Volume (%) | Matrix Tensile Strength (psi)] MD | Matrix Tensile Strength (psi) TD |
|---|---|---|---|---|---|
| Example 1 | 19.72 | 0.208 | 1.402 | 33261 | 14423 |
| Example 2 | 14.53 | 0.149 | 6.160 | 26539 | 8327 |
| Example 3 | 36.19 | 0.268 | 13.77 | 11826 | 18583 |
| Example 4 | 30.99 | 0.029 | 10.19 | 6348 | 9798 |
| Comparative Example | 17.47 | 0.609 | 2.658 | 39141 | 17136 |

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:
1. A dense article comprising:
   a TFE copolymer film having a first endotherm between about 50° C. and about 300° C., a second endotherm between about 320° C. and about 330° C., and a third endotherm between about 350° C. and about 400° C.,
   wherein said TFE copolymer comprises a core shell TFE copolymer and said core shell TFE copolymer comprises at least 3.0% by weight polymerized units of at least one comonomer based on a total weight of said core shell TFE copolymer.
2. The dense article of claim 1, wherein said third endotherm is about 380° C.
3. The dense article of claim 1, wherein said TFE copolymer comprises at least 40% TFE monomers.
4. The dense article of claim 1, wherein said dense article has a methane permeability less than about 20 μg*micron/cm²/min.
5. The dense article of claim 1, wherein said dense article has a void volume of less than about 20%.
6. The dense article of claim 1, wherein said dense article has a void volume of less than about 10%.
7. The dense article of claim 1, wherein said dense article has a void volume of less than about 5%.
8. The dense article of claim 1, wherein said core shell TFE copolymer is blended with at least 5% by weight of a member selected from the group consisting of a tetrafluoroethylene (TFE) homopolymer, a thermoplastic polymer, a further TFE copolymer and combinations thereof.
9. The dense article of claim 8, wherein said thermoplastic polymer comprises a member selected from the group consisting of fluorinated ethylene propylene (FEP), polyvinylidene fluoride (PVDF), a copolymer of TFE and perfluoro(alkyl vinyl) ether (PAVE), perfluoroelastomeric materials (FFKM), a polymer of tetrafluoroethylene, hexafluoropropylene, and vinylidene fluoride (THV), perfluoroalkoxy alkane (PFA), a copolymer of ethylene and tetrafluoroethylene (ETFE), and polychlorotrifluoroethene (PCTFE).
10. A laminate comprising:
   a dense TFE copolymer film having a first endotherm between about 50° C. and about 300° C., a second endotherm between about 320° C. and about 330° C., and a third endotherm between about 350° C. and about 400° C.; and
   a substrate,
   wherein said TFE copolymer comprises a core shell TFE copolymer and said core shell TFE copolymer comprises at least 3.0% by weight polymerized units of at least one comonomer based on a total weight of said core shell TFE copolymer.
11. The laminate of claim 10, wherein said substrate is a member selected from the group consisting of fluorinated ethylene propylene (FEP), perfluoroalkoxy alkane (PFA), polytetrafluoroethylene (PTFE), a polymer of tetrafluoroethylene, hexafluoropropylene, and vinylidene fluoride (THV), polyurethanes, polyamides, ethylene vinyl alcohol (EVOH), polyvinyl chloride (PVC), a metallic sheet, an inorganic sheet and a pressure sensitive adhesive.
12. A laminate comprising:
   a dense article comprising a TFE copolymer film having a first endotherm between about 50° C. and about 300°

C., a second endotherm between about 320° C. and about 330° C., and a third endotherm between about 350° C. and about 400° C.; and a substrate, wherein said TFE copolymer comprises a core shell TFE copolymer and said core shell TFE copolymer comprises at least 3.0% by weight polymerized units of at least one comonomer based on a total weight of said core shell TFE copolymer.

13. The laminate of claim 12, wherein said TFE copolymer film has been compressed into a dense TFE copolymer film.

14. The laminate of claim 12, wherein said TFE copolymer film has been compressed and subsequently stretched.

15. The laminate of claim 12, wherein said substrate is a member selected from the group consisting of fluorinated ethylene propylene (FEP), perfluoroalkoxy alkane (PFA), polytetrafluoroethylene (PTFE), a polymer of tetrafluoroethylene, hexafluoropropylene, and vinylidene fluoride (THV), polyurethanes, polyamides, ethylene vinyl alcohol (EVOH), polyvinyl chloride (PVC), a metallic sheet, an inorganic sheet and a pressure sensitive adhesive.

16. A dense article comprising:
a TFE copolymer film having a first endotherm between about 50° C. and about 300° C., a second endotherm between about 320° C. and about 350° C., and a third endotherm at approximately 380° C., wherein said TFE copolymer comprises a core shell TFE copolymer and said core shell TFE copolymer comprises at least 3.0% by weight polymerized units of at least one comonomer based on a total weight of said core shell TFE copolymer.

17. The dense article of claim 16, wherein said second endotherm is between about 320° C. and about 330° C.

18. The dense article of claim 16, wherein said second endotherm is between about 330° C. and about 350° C.

19. The dense article of claim 16, wherein said TFE copolymer comprises at least 40% TFE monomers.

20. The dense article of claim 16, wherein said dense article has a methane permeability less than about 20 µg*micron/cm²/min.

21. The dense article of claim 16, wherein said dense article has a void volume of less than about 20%.

22. The dense article of claim 16, wherein said core shell TFE copolymer is blended with at least 5% by weight of a member selected from the group consisting of a tetrafluoroethylene (TFE) homopolymer, a thermoplastic polymer, a further TFE copolymer and combinations thereof.

23. The dense article of claim 22, wherein said thermoplastic polymer comprises a member selected from the group consisting of fluorinated ethylene propylene (FEP), polyvinylidene fluoride (PVDF), a copolymer of TFE and perfluoro(alkyl vinyl) ether (PAVE), perfluoroelastomeric materials (FFKM), a polymer of tetrafluoroethylene, hexafluoropropylene, and vinylidene fluoride (THV), perfluoroalkoxy alkane (PFA), a copolymer of ethylene and tetrafluoroethylene (ETFE), and polychlorotrifluoroethene (PCTFE).

24. A laminate comprising:
a dense TFE copolymer film having a first endotherm between about 50° C. and about 300° C., a second endotherm between about 320° C. and about 350° C., and a third endotherm at approximately 380° C.; and a substrate, wherein said TFE copolymer comprises a core shell TFE copolymer and said core shell TFE copolymer comprises at least 3.0% by weight polymerized units of at least one comonomer based on a total weight of said core shell TFE copolymer.

25. The laminate of claim 24, wherein said substrate is a member selected from the group consisting of fluorinated ethylene propylene (FEP), perfluoroalkoxy alkane (PFA), polytetrafluoroethylene (PTFE), a polymer of tetrafluoroethylene, hexafluoropropylene, and vinylidene fluoride (THV), polyurethanes, polyamides, ethylene vinyl alcohol (EVOH), polyvinyl chloride (PVC), a metallic sheet, an inorganic sheet and a pressure sensitive adhesive.

26. A laminate comprising:
a dense article comprising a TFE copolymer film having a first endotherm between about 50° C. and about 300° C., a second endotherm between about 320° C. and about 350° C., and a third endotherm at approximately 380° C.; and a substrate, wherein said TFE copolymer comprises a core shell TFE copolymer and said core shell TFE copolymer comprises at least 3.0% by weight polymerized units of at least one comonomer based on a total weight of said core shell TFE copolymer.

27. The laminate of claim 26, wherein said TFE copolymer film has been compressed into a dense TFE copolymer film.

28. The laminate of claim 26, wherein said TFE copolymer film has been compressed and subsequently stretched.

29. The laminate of claim 26, wherein said substrate is a member selected from the group consisting of fluorinated ethylene propylene (FEP), perfluoroalkoxy alkane (PFA), polytetrafluoroethylene (PTFE), a polymer of tetrafluoroethylene, hexafluoropropylene, and vinylidene fluoride (THV), polyurethanes, polyamides, ethylene vinyl alcohol (EVOH), polyvinyl chloride (PVC), a metallic sheet, an inorganic sheet and a pressure sensitive adhesive.

* * * * *